(12) United States Patent
Siret et al.

(10) Patent No.: US 9,175,034 B2
(45) Date of Patent: Nov. 3, 2015

(54) METHOD FOR PURIFYING OR DETECTING A TARGET PROTEIN

(75) Inventors: Laurent Siret, Villiers sur Orge (FR);
Abdessatar Chtourou, Elancourt (FR);
Frédéric Dhainaut, Boissy le Sec (FR);
Gérald Perret, Choisy le Roi (FR)

(73) Assignee: LABORATOIRE FRANCAIS DU FRACTIONNEMENT ET DES BIOTECHNOLOGIES, Les Ulis (FR)

( * ) Notice: Subject to any disclaimer, the term of this patent is extended or adjusted under 35 U.S.C. 154(b) by 160 days.

(21) Appl. No.: 12/673,661

(22) PCT Filed: Aug. 13, 2008

(86) PCT No.: PCT/FR2008/051495
§ 371 (c)(1),
(2), (4) Date: Feb. 16, 2010

(87) PCT Pub. No.: WO2009/024726
PCT Pub. Date: Feb. 26, 2009

(65) Prior Publication Data
US 2011/0097715 A1  Apr. 28, 2011

(30) Foreign Application Priority Data

Aug. 14, 2007  (FR) .................................... 07 57072

(51) Int. Cl.
*C07H 21/04* (2006.01)
*C12P 21/00* (2006.01)
*C07K 1/22* (2006.01)
*C12N 15/115* (2010.01)
*G01N 33/86* (2006.01)

(52) U.S. Cl.
CPC ................ *C07K 1/22* (2013.01); *C12N 15/115* (2013.01); *G01N 33/86* (2013.01); *G01N 2333/755* (2013.01); *G01N 2333/974* (2013.01)

(58) Field of Classification Search
CPC . C12N 15/115; G01N 33/86; G01N 2333/755
See application file for complete search history.

(56) References Cited

U.S. PATENT DOCUMENTS

| 5,965,789 | A  | * | 10/1999 | Lubon et al. ..................... 800/14 |
| 6,794,148 | B2 | * | 9/2004 | Jindal et al. ..................... 435/7.1 |
| 7,741,307 | B2 | * | 6/2010 | Sullenger et al. ........... 514/44 R |
| 2005/0089893 | A1 | * | 4/2005 | Lopez et al. ....................... 435/6 |
| 2006/0057573 | A1 | * | 3/2006 | Gold et al. ......................... 435/6 |
| 2009/0170219 | A1 |   | 7/2009 | Nakamura et al. |

FOREIGN PATENT DOCUMENTS

| EP | 1918372 A | 7/2008 |
| WO | 02/26932 A | 4/2002 |
| WO | 2005/024042 A | 3/2005 |
| WO | 2007/004748 A | 1/2007 |

OTHER PUBLICATIONS

Wang et al. (Journal of Biotechnology 102, 2003, 15-22).*
Bock et al. Nature 355, 1992, 564-566.*
Colman (Am. J. Clin. Nutr. 1996;63:639S-45S).*
Hutanu et al. Adv Chromatogr. 2007;45:173-96.*
Romig et al. J Chromatogr B Biomed Sci Appl. Aug. 20, 1999;731(2):275-84.*
Ciara O'Sullivan Anal Bioanal Chem 2002, 372:44-48.*
Ravelet et al. Journal of Chromatography A 1117, 2006, 1-10.*
Liu Xuemei et al,"RNA aptamers specific for bovine thrombin", Journal of Molecular Recognition: JMR, Jan.-Feb. 2003, pp. 23-27, vol. 16, No. 1, XP002479553.
Surugiu-Warnmark I et al, "Selection of DNA aptamers against rat liver X receptors", Biochemical and Biophysical Research Communications, Jul. 1, 2005, pp. 512-517, vol. 332, No. 2, Academic Press . Inc. Orlando, FL, US, XP004902506.
Lee S K et al, "An RNA aptamer that binds to the beta-catenin interaction domain of TCF-I protein", Biochemical and Biophysical Research Communications, Feb. 4, 2005, pp. 294-299, Academic Press Inc. Orlando, FL, US, vol. 327 , No. 1, XP004697926.
International Search Report in Corresponding Application No. PCT/FR2008/051495 Dated Mar. 11, 2009.

* cited by examiner

*Primary Examiner* — Brian Whiteman
(74) *Attorney, Agent, or Firm* — Foley & Lardner LLP (57) ABSTRACT

A method for purifying or detecting a target protein present in a solution, includes, before carrying out the actual detection or purification step, a step of contacting the solution with an aptamer binding specifically to the target protein, where the aptamer does not bind to a protein homologous to the target protein that could also be present in the solution.

18 Claims, 4 Drawing Sheets

SEQUENCE LISTING

<160> NUMBER OF SEQ ID NOS: 1

<210> SEQ ID NO 1
<211> LENGTH: 68
<212> TYPE: RNA
<213> ORGANISM: Artificial Sequence
<220> FEATURE:
<223> OTHER INFORMATION: Synthetic Oligonucleotide

<400> SEQUENCE: 1
gggagagagg aagagggaug ggagccuaug uaacagaugc agaucccuag ucgucccaac      60
accauaac                                                              68

METHOD FOR PURIFYING OR DETECTING A TARGET PROTEIN

FIELD OF THE INVENTION

The present invention relates to the field of purification and detection of proteins. The invention especially relates to the use of an aptamer for specifically purifying or detecting proteins of interest in media, in particular in solutions, that may also comprise proteins homologous to the proteins of interest.

PRIOR ART

Methods for purifying and detecting a protein of interest, which may also be referred to as a "target protein", typically comprise a step of contacting the medium to be tested, that may contain the protein of interest, with compounds able to bind to the said protein of interest. Such compounds that can bind to a target protein may have various natures. They may be either (i) organic compounds comprising chemical groups possessing properties of binding to proteins (such as DEAE, quaternary ammonium, alkyl chain, silanol), (ii) or proteins (such as antibodies), glycosaminoglycans (heparin), dyes (cibacron blue F3GA) or nucleic acids (such as aptamers).

The efficiency of a method for purifying or detecting a target protein depends amongst others on the affinity and specificity of the compound which binds to the target protein.

With some starting media having a complex composition, especially starting solutions comprising many distinct proteins, it remains difficult to purify and to detect a target protein of interest. That is especially the case with complex starting media wherein a target protein to purify or to detect does coexist with one or more proteins that are distinct but highly homologous one to each other. Indeed, when the target protein is present in the solution together with one or more proteins homologous to this target protein, it then becomes difficult to develop purification or detection tools enabling a high discrimination level between the target protein of interest and the unwanted homologous protein(s), by using purification or detection conventional methods. Even antibodies, which are known for their high specificity towards target proteins, often suffer from a cross reactivity, including with many proteins having structure homology to the target proteins.

The difficulty to purify or detect specifically proteins that are homologous to each other is a drawback in a number of application fields, both in the academic research field aiming at specifically studying a target protein regardless of any other protein that would be potentially homologous to the target protein, or in the industrial field, for example for developing new, more efficient purification or detection tools and, in that event, having an improved compatibility with regulation or administrative requirements, as compared to known purification or detection tools.

The difficulty for purifying or detecting specifically proteins that are homologous to each other occurs when a protein (being herein referred to as transgenic protein) is prepared in a recombinant form in a transgenic organism or microorganism that also naturally expresses a protein homologous to said transgenic protein. Involved are especially recombinant proteins obtained from organisms inherently possessing in their genome a gene said to be "orthologous" encoding a protein that is highly homologous to the recombinant protein encoded by a transgene.

It is usual for a human or an animal transgenic protein expressed in a transgenic animal to be homologous to an endogenous protein that is naturally expressed in the transgenic animal. Producing the natural, endogenous homologous protein is technically problematic in the situations where a co-extraction or a co-detection of the transgenic protein and of the natural, endogenous homologous protein should be avoided.

When the transgenic recombinant protein is a protein of therapeutic interest, to be used for making a drug, the presence, in the recombinant protein purified preparation, of any endogenous protein homologous to the transgenic protein may cause unwanted adverse effects in the patient to whom the drug has been administered, including the induction of an unwanted immune response to the contaminating natural protein, which may impair the efficiency of the medical treatment and sometimes even lead to autoimmune responses which nature could be potentially harmful to the patient health. Such difficulties arise more and more frequently because of the increasing use of therapeutic transgenic proteins produced in transgenic animals. To make highly safe therapeutic products available, the transgenic proteins should thus be specifically purified, in the presence of very small amounts of unwanted homologous proteins, and if possible in the complete absence of unwanted homologous proteins. Indeed, the methods for detecting the target proteins of interest should be specific, sensitive and efficient.

Aptamers of the RNA type, single stranded ribonucleic acid molecules, selected according to a method known as SELEX, can specifically bind to proteins of interest. In the publication of Liu and al. *RNA aptamers specific for bovine thrombin*, J. Mol. Recognit., 2003:16, 23-27, the author presents an aptamer of the RNA type which binds to bovine thrombin but not to human thrombin. This article, although isolated, shows that it is possible through the SELEX method to select highly specific RNA aptamers that are able to discriminate homologous proteins in a solution.

However, no industrial process using highly specific aptamers for discriminating homologous proteins has been described in the literature to this day.

Using highly specific aptamers raises many technical problems. First of all, aptamers are selected in a solution through the SELEX method. For being suitably used in a purification or a detection method, the aptamer should be immobilized onto a solid support. And yet many publications show that the aptamer binding properties (affinity, specificity . . . ) are impaired when the aptamer is immobilized. In addition, aptamers of the RNA type, the only highly specific aptamer type that has been described in the prior art, are very labile molecules which undergo alteration at room temperature. RNA aptamers are thus not compatible with industrial purification or detection processes. Chemically modified RNA could represent an alternative but the current synthesis costs for such molecules are indisputably incompatible with industrial scale applications.

Because of their strong affinity and of their relatively high specificity for proteins of interest, antibodies are broadly used in protein purification and detection methods.

However, using antibodies does not always suit the purification or the detection of a target protein. Indeed antibodies are prepared in biological systems with all intrinsic drawbacks, including the risks of contamination through pathogens, or the difficulty to purify engineered antibodies. In addition, antibodies are typically immunogenic and may induce strong immune reactions when administered to a patient. Thus, when an antibody is used for purifying a therapeutic protein, there is a risk for antibodies or antibody fragments to remain in the therapeutic protein-containing solution and hence to cause unwanted reactions in the patient to whom such a solution has been administered. That is the reason why using antibodies in purification methods has become hardly compatible with some administrative requirements, in particular in the agri-food and pharmaceuticals industries. Moreover it should be added that with antibodies, sanitization means are limited, because of their sensitive protein nature, especially (i) under denaturing conditions (for example in the presence of urea, of DMSO, etc.), (ii) with highly acidic or basic pH values, (iii) with some deleterious organic solvents or (iv) under high temperatures. Finally, it is herein reminded that selecting an antibody is a long-lasting process (approx. 6 months) and that obtaining a purified antibody is a complicated task, inducing relatively high selection and preparation costs.

There is hence a need for developing novel purification or detection tools for proteins of interest, which would be efficient, readily implementable and more reliable, as compared to the known methods. Such improved methods should enable the selective purification or detection of a target protein that is present in a solution when said solution may also contain a protein homologous to the target protein. More particularly, there is a need for developing new purification or detection tools that are able to improve the human safety and security conditions towards products resulting from the production of therapeutic transgenic proteins derived from transgenic organisms.

SUMMARY OF THE INVENTION

It is an object of the present invention to provide a method for purifying or detecting a target protein present in a solution, the said method comprising, before carrying out the detection or purification step, a step of contacting the said solution with a DNA aptamer immobilized onto a solid support through a spacer, the said immobilized aptamer binding specifically to the said target protein but not to any protein homologous to the said target protein that could also be present in the solution.

The present invention hence also relates to the use of a DNA aptamer immobilized onto a solid support through a spacer, said immobilized aptamer binding specifically to a target protein, for purifying or detecting said target protein present in a solution, characterized in that said immobilized aptamer does not bind to a protein homologous to said target protein and that said solution may contain at least one protein homologous to said target protein.

The present invention also relates to a method for purifying specifically a target protein from a solution containing said target protein and that may contain a protein homologous to said target protein, comprising the steps of (i) providing a solid support comprising a DNA aptamer immobilized onto said solid support through a spacer, characterized in that said immobilized aptamer does specifically bind to said target protein but not to a protein homologous to said target protein, (ii) contacting said solid support with said solution, and (iii) recovering the target protein bound to said aptamer.

The present invention further relates to a method for detecting specifically a target protein from a solution which contains said target protein and which may contain a protein homologous to said target protein, comprising the steps of (i) contacting said solution with a DNA aptamer immobilized onto a solid support through a spacer, said immobilized aptamer binding specifically to said target protein but not to said protein homologous to the target protein, and (ii) detecting the complexes formed between said aptamer and said target protein.

DESCRIPTION OF THE FIGURES

FIG. 1 represents a graph illustrating the binding, as a function of time between the human anti-FVII aptamer and HP FVII, with HP FVII concentrations ranging from 50 to 400 nM.

FIG. 2 represents a graph illustrating the binding, as a function of time, between the aptamer which does specifically bind to human factor VII immobilized onto a chip and HP FVII in the presence of a polyclonal anti-FVII antibody, or in the absence thereof.

FIG. 3 represents a graph illustrating the binding, as a function of time, between the aptamer which does specifically bind to human factor VII and rabbit plasma-derived factor VII, with rabbit factor VII concentrations ranging from 50 to 400 nM.

FIG. 4 represents a graph illustrating the binding, as a function of time, between the aptamer which does specifically bind to human factor VII and HP FVII, rabbit factor VII or transgenic human factor VII, with a concentration of 400 nM for each FVII.

DESCRIPTION OF THE INVENTION

The present invention provides a method for purifying or detecting a target protein present in a solution, said method comprising, before carrying out the detection or purification step, a step of contacting said solution with a DNA aptamer immobilized onto a solid support through a spacer, said immobilized aptamer binding specifically to said target protein but not to any protein homologous to said target protein that could also be present in the solution.

The invention further relates to the use of a DNA aptamer immobilized onto a solid support through a spacer, said immobilized aptamer binding specifically to a target protein, for purifying or detecting said target protein present in a solution, characterized in that said immobilized aptamer does not bind to a protein homologous to said target protein and that said solution may contain at least one protein homologous to said target protein.

In the method for purifying a target protein of interest, a complex is selectively formed between (i) said aptamer recognizing specifically a given target protein and (ii) the target protein, when this one is contained in the starting medium, typically the starting solution. Thereafter, the target protein to be purified is recovered upon dissociation of the complex formed beforehand with said aptamer.

In the method for detecting a target protein of interest, a complex is selectively formed between (i) said aptamer recognizing specifically a given target protein and (ii) the target protein, when this one is contained in the starting medium, typically the starting solution. Thereafter are detected especially (i) either the complexes formed between said aptamer and said protein of interest, (ii) or the target protein of interest, either complexed with said aptamer or in a free form after dissociation of the previously formed complexes.

It is another object of the present invention to provide a method for purifying specifically a target protein from a solution which contains said target protein and which may contain a protein homologous to said target protein, comprising the steps of:

a) providing a solid support comprising a DNA aptamer immobilized onto said solid support through a spacer, characterized in that said immobilized aptamer does specifically bind to said target protein but not to a protein homologous to said target protein,
  b) contacting said solid support with said solution, and
  c) recovering the target protein bound to said aptamer.

It is a further object of the present invention to provide a method for detecting specifically a target protein from a solution which contains said target protein and which may contain a protein homologous to said target protein, comprising the steps of:

a) contacting said solution with a DNA aptamer immobilized onto a solid support through a spacer, said immobilized aptamer binding specifically to said target protein but not to said protein homologous to said target protein, and
  b) detecting the complexes formed between said aptamer and said target protein.

As used herein, an "aptamer" is intended to mean a single-stranded nucleic acid molecule which can bind specifically to a protein. Aptamers comprise typically from 5 to 120 nucleotides and may be selected in vitro through a method known as SELEX (Systematic Evolution of Ligands by Exponential Enrichment). Aptamers have many advantages. Due to their oligonucleotide nature, aptamers possess a low immunogenicity and are highly resistant to stringent physico-chemical conditions (presence of urea, DMSO, highly acidic or basic pH values, use of organic solvents or high temperatures) making it possible to implement diversified sanitization strategies, when used as affinity ligands. In addition, they are highly selective. Finally, producing aptamers generates relatively moderate costs.

As used herein, a "DNA aptamer" is intended to mean an aptamer composed of desoxyribonucleotides, as opposed to RNA aptamers which are composed of ribonucleotides. DNA aptamers are advantageously stable in a solution, and hence can find industrial applications in the purification or detection of target proteins.

As used herein, a "protein" is intended to mean an amino-acid polymer. This includes proteins, protein fragments, genetically modified proteins, oligopeptides and analogues thereof. The protein may be an antibody, an antiviral protein, a hormone, a growth factor, a coagulation factor such as factor VII (FVII), factor VIII (FVIII), factor X (FX), factor IX (Factor IX), factor XI (FXI), factor XII (FXII), factor XIII (FXIII), factor II (thrombin), antithrombin III (AT III), heparin cofactor II (HCII), protein C(PC), thrombomodulin (TM), protein S (PS), factor V (FV), von Willebrand factor (FvW) and tissue factor pathway inhibitor (TFPI). Preferably, the protein is a native or a modified factor VII, or a fragment thereof.

As previously stated, a "DNA aptamer immobilized onto a solid support through a spacer" (also referred to as "aptamer" thereafter) is used in the methods of the invention, that is able to bind selectively to a given target protein, said aptamer having a reduced ability or no ability to bind to proteins that are "homologous" to said given target protein. This means that, according to the invention, it is made use exclusively of aptamers that have outstanding discrimination capacities between the target protein of interest and proteins that are distinct from said target protein although they have a structure close to that of said target protein.

In some embodiments of the invention, the ability of the aptamer used to discriminate the target protein from proteins that are "homologous" to the target protein is such that said aptamer has an affinity for the target protein of interest defined by a dissociation constant value (Kd), expressed in molar concentration, which is lower by at least one order of magnitude as compared to the dissociation constant value of said aptamer towards the closest known "homologous" protein.

In some other embodiments of the invention, the aptamer does not bind to a protein "homologous" to the target protein of interest. According to the invention, an aptamer does not bind to a protein homologous when the binding of the protein homologous to said aptamer cannot be detected through conventional measurement means, for example according to detection and binding measurement technologies of the Biacore® type. As an illustration, it has been shown in the examples that the aptamer of SEQ ID No. 1, which does bind selectively to human Factor VII, does not bind in a detectable manner to rabbit factor VII, when using the binding measurement system Biacore®.

The "target protein" to which the aptamer does bind selectively may be any kind of protein. The target protein may especially be a protein of therapeutic interest.

The "homologous protein" or "the protein homologous to the target protein" means a protein which possesses a strong structural homology with the target protein.

As used herein, "homology" is intended to substantially mean two types of homologies, respectively (i) a homology resulting from differences in the amino-acid sequence between the target protein and the homologous protein and (ii) a homology resulting from differences in the additional chemical groups that are covalently bound onto the amino-acid side chains, including differences in the osidic chains. It will become clearly apparent to the person skilled in the art that the target protein of interest and a "homologous" protein may differ from each other both relative to differences in the amino-acid sequence and to differences in the osidic chains. As an illustration, the two types of structural differences may be encountered when a difference in the amino-acid sequence occurs on an amino-acid consisting in a glycosylation site of the target protein or of the homologous protein.

According to the invention, the given target protein and a corresponding homologous protein comprise sequences which possess at least 50% amino acid identity with each other. According to the invention, the identity percentage between two amino-acid sequences or between two nucleotide sequences may be calculated by using the Emboss matcher, EBLOSUM62 with the default parameters, amongst which Gap_penalty: 10.0 and Extend_penalty: 0.5.

Preferably, the amino acid sequence identity between the target protein and the homologous protein is at least 50%, 55%, 60%, 65%, 70%, 75%, 80%, 85%, 90%, 91%, 92%, 93%, 94%, 95%, 96%, 97%, 98% or 99%.

As previously indicated, the difference between the target protein of interest and the homologous protein may result from glycosylation differences between both proteins. A difference in glycosylation relates to two proteins having the same amino-acid sequence or having similar amino-acid sequences but different glycan structures. The glycan structures are sugar chains that are grafted onto proteins at amino-acid consensus sequences. The glycosylation differences may relate to N- or O-glycosylations as well as to glycoside branching occurring upon N- or O-glycosylations. The difference in glycosylation may relate to the presence or the absence of such chains or branching but also to the presence or the absence of some sugars such as fucose, mannose, glucosamine or galactosamine residues. Protein glycosylation may be analyzed in a number of ways. A glycosylation analysis method consists in deglycosylating a protein through the use of one or more enzymes (PNGaseF, N-glycosidase) or via a chemical route (hydrazynolysis, β-elimination), then in directly analyzing the glycans obtained on gel, capillary electrophoresis or HPLC (with an ultraviolet, fluorescent or MS detection) or in analyzing after an enzyme-mediated depolymerization (neuraminidase and (-galactosidase) or a chemically induced depolymerization (hydrazynolysis, β-elimination) in order to sequence said glycans. Another analysis method consists in using mass spectrometry on the whole protein, these techniques being known as MALDI (Matrix-Assisted Laser Desorption/Ionization), MALDI-TOF (Time Of Flight), ESI (Electrospray Ionization).

In some embodiments of the invention, an aptamer according to the invention consists in an aptamer which does specifically bind to a coagulation factor selected from factor VII (FVII), factor VIII (FVIII), factor X (FX), factor IX (Factor IX), factor XI (FXI), factor XII (FXII), factor XIII (FXIII), factor II (THROMBIN), antithrombin III (AT III), heparin cofactor II (HCII), protein C (PC), thrombomodulin (TM), protein S (PS), factor V (FV), von Willebrand factor (FvW) and tissue factor pathway inhibitor (TFPI). Advantageously, the aptamer does specifically bind to FVII. Preferably, the aptamer according to the invention does specifically bind to human factor VII but does not bind to rabbit factor VII. Conversely an aptamer according to the invention does bind to rabbit factor VII but does not bind to human factor VII.

An aptamer which does specifically bind to human factor VII but which does not bind to rabbit factor VII may be an aptamer comprising a nucleotide sequence having at least 80% nucleotide identity with the sequence SEQ ID no 1.

Advantageously, the aptamer of the invention does bind to the target protein with an affinity characterized by a dissociation constant value (Kd) ranging from 1 pM to 10 µM, preferably ranging from 10 nM to 10 µM. Advantageously, the affinity of the aptamer for the target protein is 1000 to 10 000 times higher than the affinity of the aptamer for the homologous protein.

In the purification or detection method according to the invention, the DNA aptamer is immobilized onto a solid support through a spacer. The aptamer immobilized onto a solid support is particularly well adapted to the detection or the purification of a target protein present in a solution.

As used herein, a "spacer" is intended to mean a molecule which is inserted between the aptamer and the solid support. Advantageously, the spacer is bound both to one end of the aptamer and to the solid support. Advantageously, such structure comprising a spacer does not immobilize directly the aptamer onto the solid support. The nature of the spacer may be chosen according to the knowledge of one skilled in the art; preferably the spacer is a non specific oligonucleotide sequence or is polyethylene glycol (PEG). When it is a non specific oligonucleotide sequence, said sequence contains preferably at least 5 nucleotides, preferably between 5 and 15 nucleotides.

For immobilizing the aptamer onto a spacer, the aptamer may be chemically modified with various chemical groups such as groups enabling to covalently immobilize the aptamer, such as thiols, amines or any other group that could react with chemical groups present on the support or groups enabling to non-covalently immobilize the aptamer, such as the biotin-streptavidin system. These techniques may also be used for immobilizing the spacer onto the solid support.

Once immobilized onto the solid support via the spacer, the aptamer is advantageously modified at the free end thereof (i.e. the end that is not bound to the spacer) thanks to, and without limitation, a chemically modified nucleotide (such as 2' omethyl or 2' fluoropyrimidine, 2' ribopurine, phosphoramidite), a reversed nucleotide or a chemical group (PEG, polycations, cholesterol). These modifications enable to protect the aptamer against enzymatic degradations.

The solid support may be an affinity chromatography column containing a gel derived from agarose or cellulose or a synthetic gel such as an acrylamide, a methacrylate or a polystyrene derivative; a chip such as a chip adapted for surface plasmon resonance; a membrane such as a polyamide, a polyacrylonitrile or a polyester membrane; a magnetic or paramagnetic bead.

Advantageously, the solution which contains the target protein and which may contain a protein homologous to said target protein is a biological solution such as a body fluid, a cell, a cell homogenate, a tissue, a tissue homogenate, an organ or a whole organism. Preferably the solution is a liquid biological solution obtained from an animal such as blood, a blood-derived product, a mammal's milk or a mammal's milk-derived product. It can be plasma, plasma cryoprecipitate, clarified milk or derivatives thereof. An animal according to the present invention is a living pluricellular, eukaryotic, organism that is devoid of chloroplast and non human. In an especially preferred embodiment, the solution is obtained from a transgenic animal. Advantageously, the solution is a mammal's milk or a transgenic mammal's milk-derived product. According to the invention, a transgenic animal is a mammal such as a cow, a goat, a female rabbit, a pig, a monkey, a rat, a mouse or a bird or an insect such as a mosquito, a fly or a silkworm. In a preferred embodiment, the transgenic animal is a transgenic mammal, preferably a transgenic female rabbit. Advantageously, the transgenic mammal produces within its mammary gland a transgenic protein under the control of a specific promoter enabling the expression of said transgenic protein in the milk of said transgenic mammal.

A method for producing a transgenic protein in the milk of a transgenic animal may comprise the following steps: a DNA molecule comprising a gene encoding the transgenic protein, this gene being under the control of a promoter of a gene encoding a protein naturally secreted in the milk (such as the casein promoter, the beta-casein promoter, the lactalbumin promoter, the beta-lactoglobulin or the whey acidic protein promoter (WAP)) is injected into the embryo of a non human mammal. The embryo is then inserted into a mammal female of the same species. Once the embryo-derived mammal is sufficiently developed, lactation is induced in the mammal, thereafter milk is collected. The milk then contains said transgenic protein.

An example of a method for producing a protein in the milk of a mammal female other than a human being is given in EP 0 527 063, the teachings of which may be reproduced for making the protein of the invention. A WAP promoter-containing plasmid is obtained by introducing a sequence comprising the WAP gene promoter, this plasmid being prepared so as to receive a foreign gene placed under the control of the WAP gene promoter. The promoter-containing plasmid and the gene encoding the protein of the invention are used for obtaining transgenic female rabbits, through microinjection into the male pronucleus of female rabbit embryos. The embryos are then transferred to the oviduct of hormonally prepared females. The presence of transgenes is revealed by Southern blot based on DNA extracted from the transgenic young rabbits that were born. Concentrations in the mammal's milk are determined through specific radioimmunologic tests.

Other documents describe methods for obtaining proteins in the milk of a mammal female other than a human being. To be mentioned are, without limitation, U.S. Pat. No. 7,045,676 (transgenic mice) and EP 1 739 170 (von Willebrand factor production in a transgenic mammal).

Thus, it is also an object of the present invention to provide the use of a DNA aptamer immobilized onto a solid support through a spacer, said immobilized aptamer binding specifically to human factor VII, for the purification or detection of said human factor VII present in the milk of a transgenic female rabbit, characterized in that said immobilized aptamer does not bind to rabbit factor VII and in that said transgenic female rabbit milk may contain rabbit factor VII.

It is a further object of the invention to provide the use of a DNA aptamer immobilized onto a solid support through a spacer, said immobilized aptamer binding specifically to rabbit factor VII, for the detection of said rabbit factor VII that could be present in the milk of a transgenic female rabbit, characterized in that said immobilized aptamer does not bind to human factor VII and in that said transgenic female rabbit milk contains human factor VII.

Human factor VII and rabbit factor VII have an amino-acid sequence homology of about 75% (as determined by BLAST).

It is a further object of the present invention to provide a method for selecting an aptamer which does specifically bind to a target protein but which does not bind to a protein homologous to said target protein, comprising the steps of:
  a) contacting an aptamer mixture with said protein homologous to the target protein under binding favorable conditions, and recovering those aptamers that did not bind to the homologous protein,
  b) contacting the aptamer mixture obtained in step a) with said target protein under binding favorable conditions,
  c) separating those unbound aptamers from those which did bind to said target protein,
  d) dissociating the aptamer-target protein pairs,
  e) amplifying the dissociated aptamers to obtain an aptamer-rich mixture which binds to the target protein but which does not bind to the protein homologous to the target protein, and
  f) repeating steps a), b), c) d), e) on as many cycles as necessary until this or those aptamer(s) is or are obtained, which bind(s) specifically to the target molecule but not to a protein homologous to said target protein.

The method for selecting an aptamer of the invention has many things in common with the SELEX method described in the prior art, but comprises in addition a so called "subtraction" step (step a). Therefore, the method of the invention is called "subtractive SELEX".

The aptamer selection SELEX method consists in contacting a protein with a DNA or RNA nucleic acid combinatory library (typically $10^{15}$ molecules), the nucleic acids not binding to the target are removed and the nucleic acids binding to the target are isolated and amplified. The method is repeated until the solution is sufficiently enriched with the nucleic acids which have a good affinity for the protein of interest (Tuerk and Gold, a "Systematic evolution of ligands by exponential enrichment: RNA ligands to bacteriophage T4 DNA polymerase" (1990) Science, 249(4968):505-10 and Ellington and Szostak, "In vitro selection of RNA molecules that bind specific ligands", (1990) Nature August 30;346(6287):818-22). Other examples of the SELEX method are given in EP 0 786 469, EP 668 931, EP 1 695 978, EP 1 493 825 which teaching may be reused for carrying out the aptamer selection method of the invention.

The separation step (step c) may be effected through any method enabling the separation of the aptamers bound to the target protein, called aptamer-target protein pairs, from the aptamers that are not bound to the target protein. The separation may be performed through many various methods that are known in the prior art. Thus, aptamer-target protein pairs can be retained onto nitrocellulose filters whereas free aptamers not. Columns specifically retaining the aptamer-target protein pairs may also be used for the separation step. Other methods may also be used like liquid-liquid extraction, gel shift assay or density gradient centrifugation. The selection of the separation method will depend on the properties of the target protein and on the aptamer-target protein pair and the decision will be taken based upon principles known from the person skilled in the art.

The dissociation step (step d) may be effected through any method enabling the dissociation of the chemical species. Advantageously, the dissociation may occur through an increase in the ionic strength or a change of the pH value.

The amplification of step e) may be effected through any method enabling to increase the amount or the number of aptamer copies. Advantageously, the amplification of an aptamer is performed through a PCR (Polymerase Chain Reaction). Advantageously, the amplification is effected either through a PCR for DNA or through a RT-PCR for RNA.

The "subtractive SELEX" method" is characterized by the step said to be a "subtraction" (step a) which enables to remove the aptamers which bind to the protein homologous to the target protein. After having performed a cycle comprising steps a), b), c), d) and e), the following cycles may either comprise steps a), b), c), d) and e) de nuevo, or may start directly from step b) with a pool of aptamers amplified in step e) of the previous cycle. Thus, the subtraction step a) is performed at the beginning of each new cycle or alternatively after having executed at least one cycle without step a) and until obtaining aptamers which bind specifically to the target protein but not to the protein homologous to the target protein. Advantageously, each step a) is performed every second or every third cycle.

The following examples illustrate the invention without limiting the scope thereof.

EXAMPLES

Example 1

Binding of the Aptamer (SEQ No 1) to the Human Factor VII

An aptamer comprising SEQ ID no 1 was synthesized by the Sigma-Proligo company.

```
SEQ n° 1:
5' PGGGAGAGAGGAAGAGGGAUGGGAGCCUAUGUAACAGAUGCAGAUCC
CUAGUCGUCCCAACACCAUAAC-3'-Biotin
```

This aptamer is modified at the 3'-end thereof by grafting a biotin. Nucleotide bases in bold (SEQ no 1) are 2'O-methylated, which makes it possible to stabilize the aptamer by making it more resistant to nucleases. The aptamer was then immobilized onto an avidin-containing SA chip (Biacore GE). The aptamer was thus immobilized in an oriented manner through the 3'-end thereof with an immobilization rate of 2700 RU (where 1 RU does approximately correspond to 1 pg of immobilized product per $mm^2$).

Figure 1:
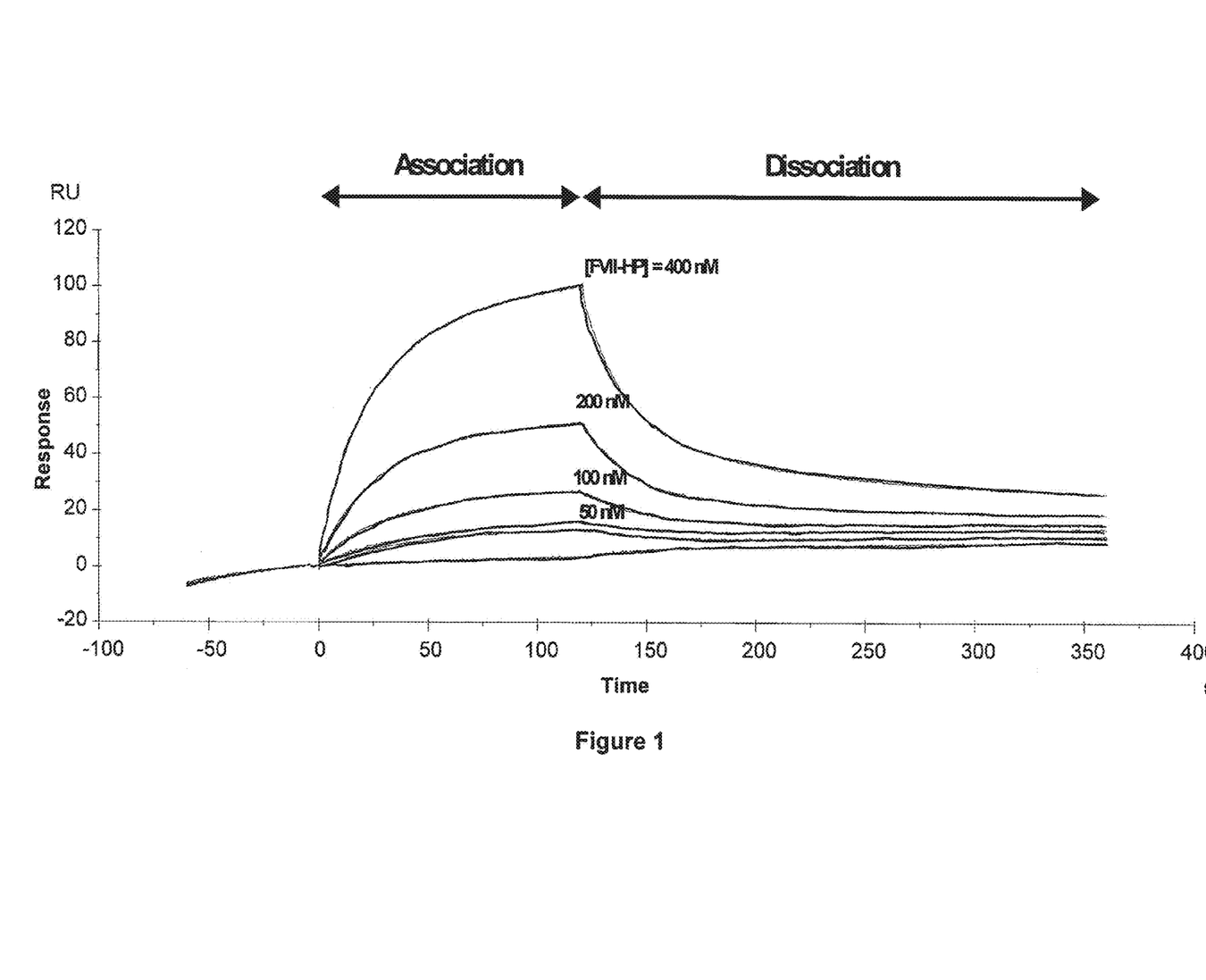
FIG. 1 shows the binding between an aptamer which does specifically bind to human factor VII and the human plasma-derived FVII (HP FVII).

Some purified, human plasma-derived factor VII (HP FVII, purity: 99%) was diluted in run buffer (Hepes 20 mM pH=8, NaCl 50 mM, $CaCl_2$ 2 mM and BSA 0.01%) so as to obtain four samples with human plasma-derived factor VII concentration levels of 50, 100, 200 and 400 nM. Each sample was injected sequentially into the same immobilized aptamer-containing chip through a biotin-streptavidin interaction. Controls are obtained by injecting blanks which only contained the run buffer. All injections are performed at a flow rate of 20 μl/min for 120 sec, after injection of the run buffer into the chip at the same flow rate for 240 sec. Some elution buffer (NaCl, 5M) was then injected for 60 seconds at a flow rate of 30 μl/min for uncoupling the human plasma-derived factor VII from the aptamer. Each injection (samples and blanks) was made in duplicate. The chip makes it possible to observe in real time the creation and the disruption of the interactions between the human plasma-derived factor VII and the immobilized aptamer through surface plasmon resonance (RPS). A binding to the immobilized aptamer generates a signal increase expressed in resonance unit (RU) recorded by the device (FIG. 1). These measures are effected with the RPS Biacore T100 apparatus (GE). The modelling of the recorded interactions was made by means of the Biaevaluation software (GE). Based on an allosteric binding modelling, the Kd value for the binding between the aptamer and HP FVII was estimated to be 1.4 μM.

Figure 2:
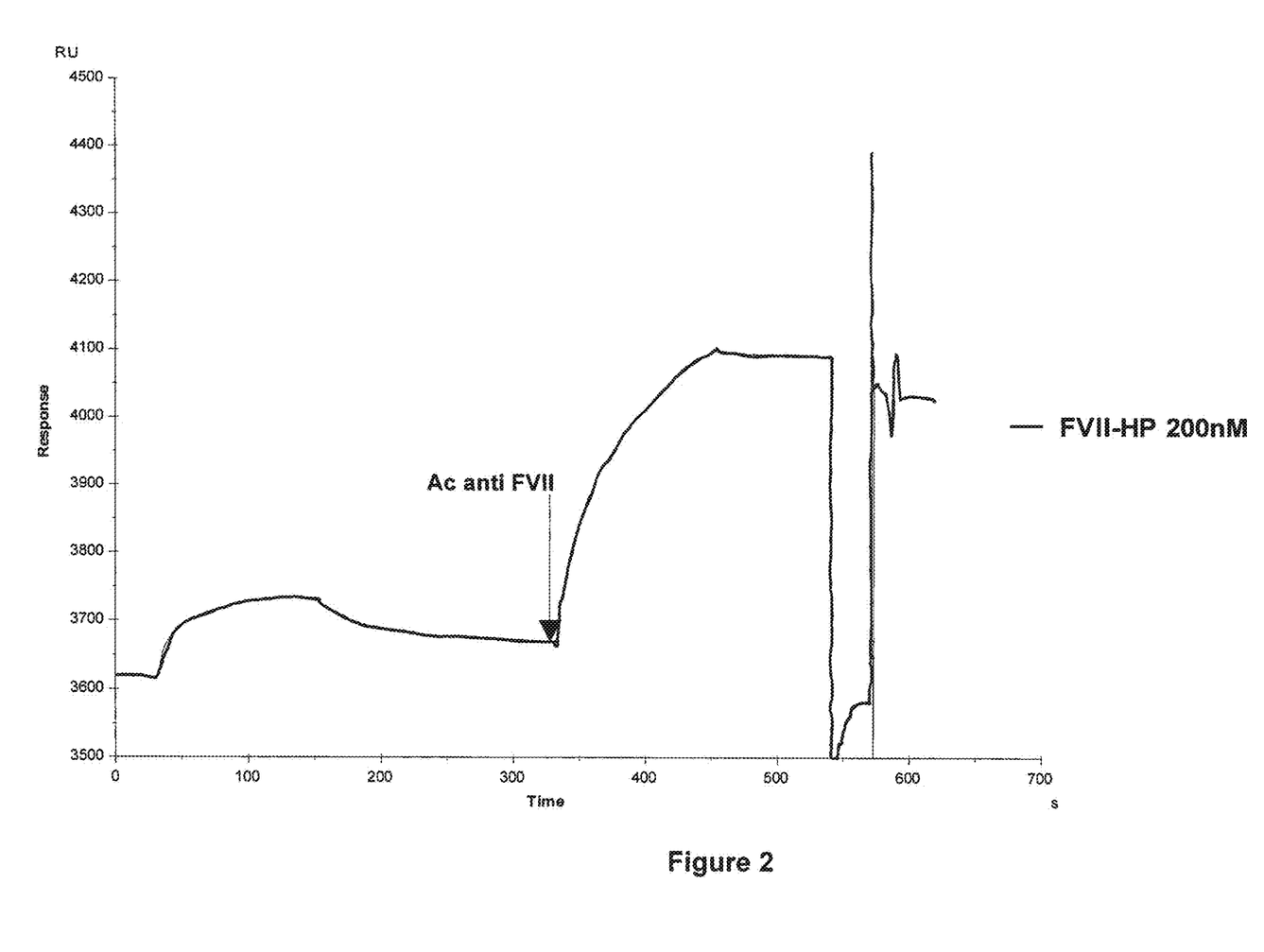
FIG. 2 shows the specificity of the interaction between an aptamer immobilized onto a chip and HP FVII.

To verify that the product which binds to the immobilized aptamer is actually factor VII, an injection sequence comprising (i) human plasma-derived factor VII 200 nM and (ii) an anti-FVII polyclonal antibody 100 nM (Abcam) was performed on the same chip. The injection and analysis conditions are the same as those described hereabove. If the aptamer retains actually FVII, the anti-FVII polyclonal antibody injection should result in a signal increase (RU) following the binding of the antibodies to FVII, with FVII itself bound to the aptamer. Antibodies alone are injected as controls. The signal increase in RU clearly shows that the aptamer recognizes FVII (FIG. 2).

This example shows that the aptamer, once immobilized, does specifically bind to the human plasma-derived factor VII, with a significant affinity.

Example 2

Binding of the Aptamer (SEQ No 1) with Rabbit Factor VII

Rabbit plasma-derived factor VII (American Diagnostica) was diluted in the same buffer as in Example 1 at concentration levels of 50, 100 200, 400 nM, thereafter was injected under the same conditions as in Example 1 into the same chip containing the immobilized aptamer.

Figure 3:
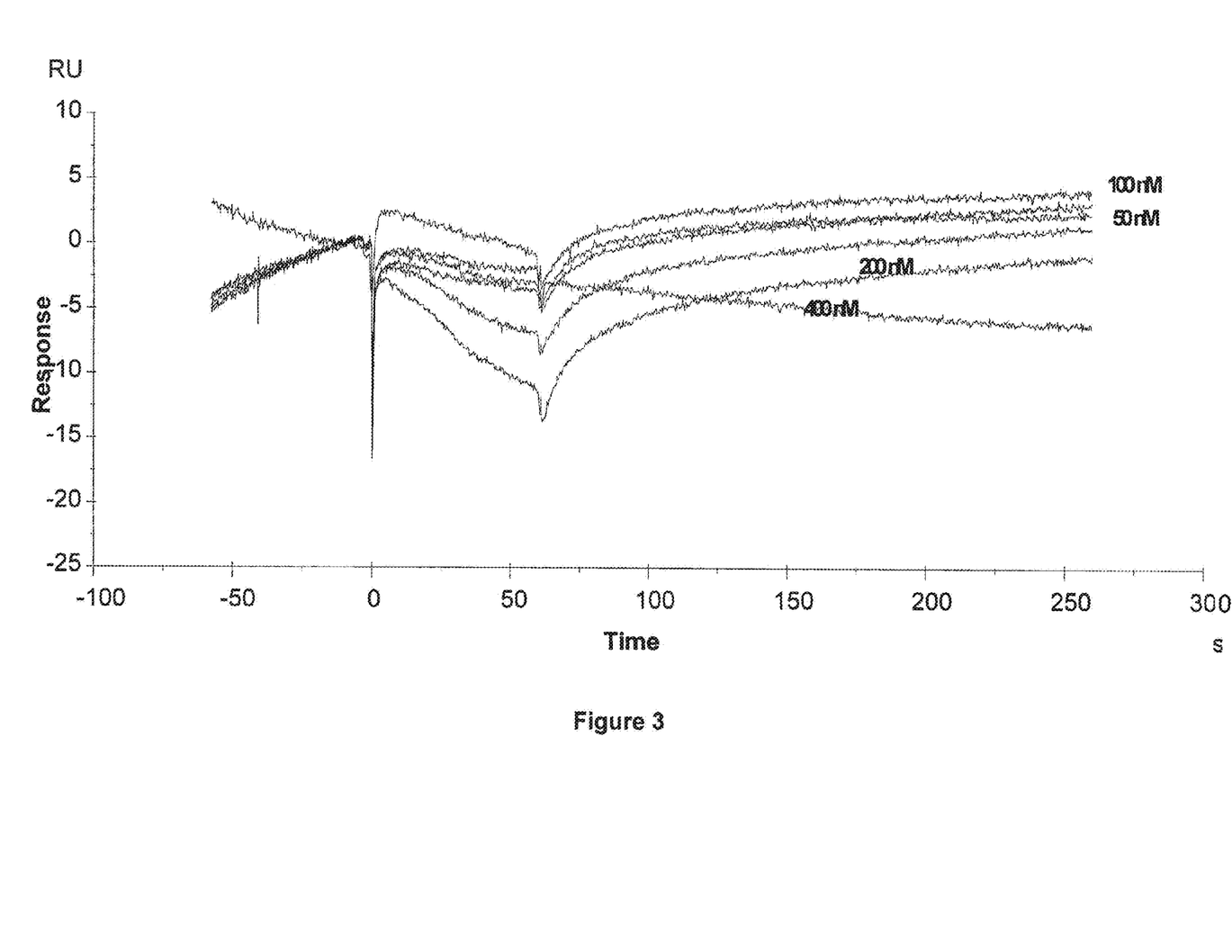
FIG. 3 shows the lack of binding between the aptamer which does specifically bind to human factor VII and rabbit plasma-derived FVII.

The recorded RU signals, shown in FIG. 3, illustrate the complete absence of binding of the aptamer to the rabbit plasma-derived FVII and that, despite a strong amino-acid sequence homology between rabbit plasma-derived FVII and human plasma-derived FVII (amino-acid sequence homology of about 75%).

This example shows that the aptamer does specifically bind to human plasma-derived FVII but does not bind to rabbit factor VII.

Example 3

Figure 4:
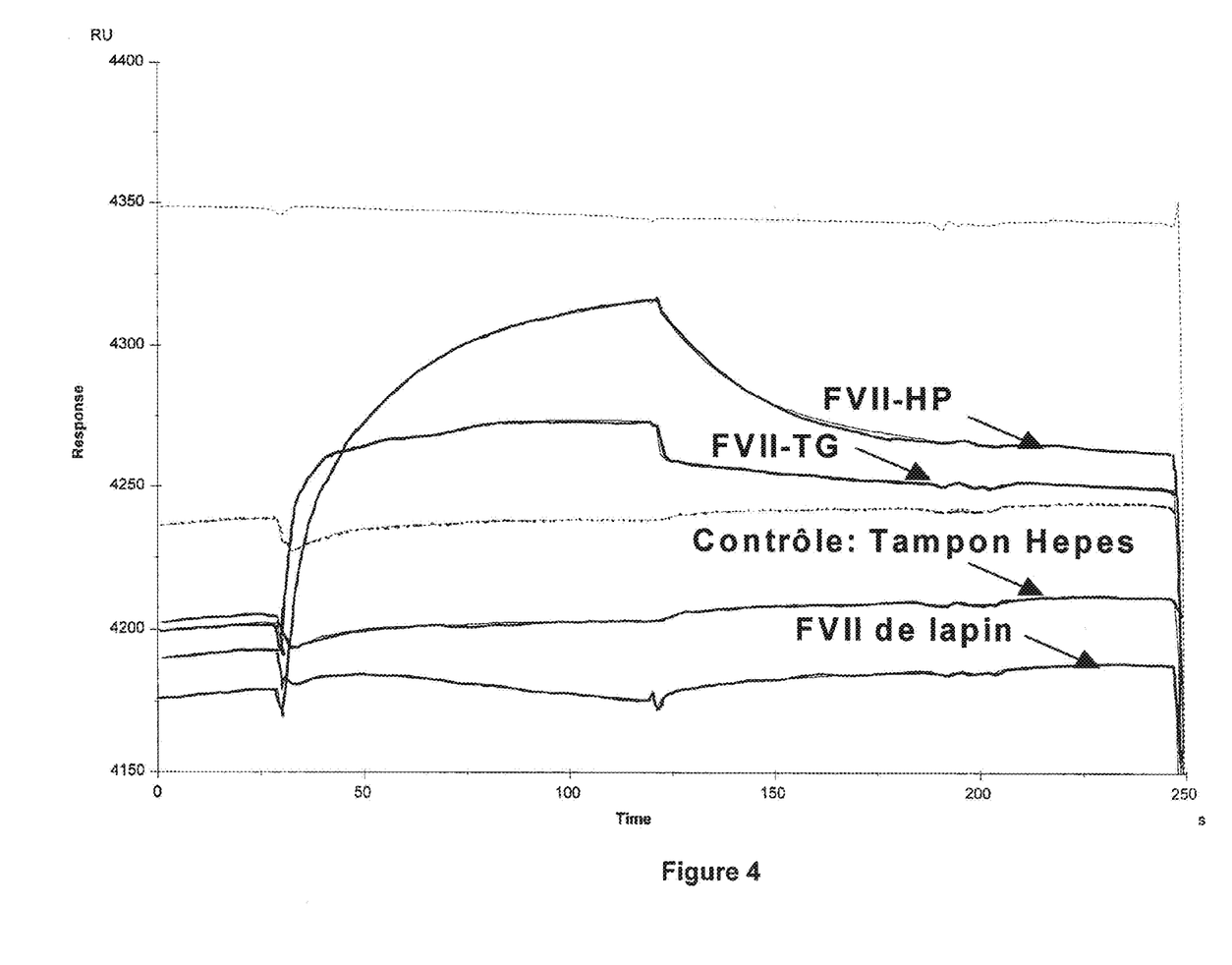
FIG. 4 shows the differences in affinity between the aptamer which does specifically bind to human factor VII and HP FVII, rabbit factor VII or transgenic human factor VII.

Differences in Affinity for the Aptamer (SEQ No 1) Between Human Plasma-Derived Factor VII, Transgenic Factor VII and Rabbit Plasma-Derived Factor VII Successive injections of human plasma-derived factor VII, rabbit plasma-derived factor VII and human transgenic factor VII were carried out under the same conditions as in Example 1 into the same chip. The data obtained (FIG. 4) show that the aptamer does bind to HP FVII and to transgenic FVII, with distinct but yet strong affinities, but does not bind to rabbit factor VII.

The invention claimed is:

1. A method for purifying a human factor VII present in a biological solution, obtained from a non-human transgenic animal, said method comprising:
contacting said biological solution with a single stranded DNA aptamer immobilized onto a solid support through a spacer, said immobilized aptamer binding specifically to said human factor VII but not to any protein homologous to said human factor VII; and then
purifying the human factor VII,
wherein said biological solution is a non-human transgenic mammal's milk, a non-human transgenic mammal's milk-derived product, or a non-human transgenic mammal's clarified milk.

2. The method according to claim 1, wherein said human factor VII has an amino-acid sequence identity of more than 50% with said homologous protein.

3. The method according to claim 1, wherein said human factor VII has a glycosylation homology with said homologous protein.

4. The method according to claim 1, wherein the aptamer comprises a nucleotide sequence at least 80% identical to SEQ ID NO:1.

5. The method according to claim 1, wherein said solid support is a chip, an affinity chromatography column, a magnetic or para-magnetic bead, or a membrane.

6. The method according to claim 1, wherein said spacer is a nonspecific oligonucleotide sequence or a sequence of a polyethylene glycol (PEG) type.

7. A method for purifying specifically a human factor VII from a biological solution, obtained from a non-human transgenic animal, which contains said human factor VII and which may contain a protein homologous to said human factor VII, comprising the steps of:
   a) providing a solid support comprising a single stranded DNA aptamer immobilized onto said solid support through a spacer, wherein said immobilized aptamer does specifically bind to said human factor VII but not to a protein homologous to said human factor VII,
   b) contacting said solid support with said biological solution, and
   c) recovering the human factor VII bound to said aptamer, wherein said biological solution is a non-human transgenic mammal's milk, a non-human transgenic mammal's milk-derived product, or a non-human transgenic mammal's clarified milk.

8. The method according to claim 7, wherein said human factor VII has an amino-acid sequence identity of more than 50% with said homologous protein.

9. The method according to claim 7, wherein the aptamer comprises a nucleotide sequence at least 80% identical to SEQ ID NO:1.

10. The method according to claim 7, wherein said solid support is a chip, a chromatography column, a magnetic or para-magnetic bead or a membrane.

11. The method according to claim 7, wherein said spacer is a non specific oligonucleotide sequence or a sequence of the a polyethylene glycol (PEG) type.

12. A method for detecting specifically a human factor VII from a biological solution, obtained from a non-human transgenic animal, which contains said human factor VII and which may contain a protein homologous to said human factor VII, comprising the steps of:
   a) contacting said biological solution with a single stranded DNA aptamer immobilized onto a solid support through a spacer, said immobilized aptamer binding specifically to said human factor VII but not to said protein homologous to said human factor VII, and
   b) detecting complexes formed between said aptamer and said human factor VII,
   wherein the aptamer comprises a nucleotide sequence at least 80% identical to SEQ ID NO:1.

13. The method according to claim 12, wherein said human factor VII has an amino-acid sequence identity of more than 50% with said homologous protein.

14. The method according to claim 12, wherein said solid support is a chip, a chromatography column, a magnetic or para-magnetic bead or a membrane.

15. The method according to claim 12, wherein said spacer is a non specific oligonucleotide sequence or a sequence of a polyethylene glycol (PEG) type.

16. The method according to claim 12, wherein said biological solution is a non-human transgenic mammal's milk, a non-human transgenic mammal's milk-derived product, or a non-human transgenic mammal's clarified milk.

17. A method for purifying a human factor VII present in a biological solution, obtained from a non-human transgenic animal, said method comprising:
   contacting said biological solution with a single stranded DNA aptamer immobilized onto a solid support through a spacer, said immobilized aptamer binding specifically to said human factor VII but not to any protein homologous to said human factor VII, wherein the aptamer comprises a nucleotide sequence at least 80% identical to SEQ ID NO:1; and then
   purifying the human factor VII.

18. A method for purifying specifically a human factor VII from a biological solution, obtained from a non-human transgenic animal, which contains said human factor VII and which may contain a protein homologous to said human factor VII, comprising the steps of:
   a) providing a solid support comprising a single stranded DNA aptamer immobilized onto said solid support through a spacer, wherein said immobilized aptamer does specifically bind to said human factor VII but not to a protein homologous to said human factor VII, and wherein the aptamer comprises a nucleotide sequence at least 80% identical to SEQ ID NO:1,
   b) contacting said solid support with said biological solution, and
   c) recovering the human factor VII bound to said aptamer.

* * * * *